US012618782B2

(12) United States Patent
Chao

(10) Patent No.: US 12,618,782 B2
(45) Date of Patent: May 5, 2026

(54) AUTOMATIC FOOD INSPECTION DEVICE

(71) Applicant: AVer Information Inc., New Taipei City (TW)

(72) Inventor: Hung Wen Chao, New Taipei City (TW)

(73) Assignee: AVer Information Inc., New Taipei City (TW)

( * ) Notice: Subject to any disclaimer, the term of this patent is extended or adjusted under 35 U.S.C. 154(b) by 37 days.

(21) Appl. No.: 18/511,989

(22) Filed: Nov. 16, 2023

(65) Prior Publication Data

US 2024/0167964 A1 May 23, 2024

(30) Foreign Application Priority Data

Nov. 17, 2022 (TW) .................................. 111144059

(51) Int. Cl.
*G01N 21/88* (2006.01)
*G01N 33/02* (2006.01)

(52) U.S. Cl.
CPC ......... *G01N 21/8851* (2013.01); *G01N 33/02* (2013.01)

(58) Field of Classification Search
CPC ............... G01N 21/8851; G01N 33/02; G01N 2021/845
See application file for complete search history.

(56) References Cited

U.S. PATENT DOCUMENTS 4,630,736 A 12/1986 Maughan et al.
2009/0184247 A1* 7/2009 Shimazu .............. G01N 21/359
250/339.11

2012/0093985 A1* 4/2012 Vasilescu .............. G06T 7/0004
382/110
2012/0188363 A1* 7/2012 Hamid ............... G01N 21/8851
348/91
2016/0109382 A1* 4/2016 Honda ............... G01N 21/8851
356/237.5
2018/0071788 A1* 3/2018 Anup ..................... G01N 21/84
2018/0080887 A1* 3/2018 Bajema .................. G01N 33/02
2018/0330490 A1* 11/2018 Kido ..................... H04N 23/62
(Continued)

FOREIGN PATENT DOCUMENTS

CN        107430141 A    12/2017
DE        10034765 A1    1/2002
(Continued)

*Primary Examiner* — Timothy R Newlin

(74) *Attorney, Agent, or Firm* — CKC & Partners Co., LLC

(57) ABSTRACT

An automatic food inspection device includes a feeding container, a track conveying device, a transparent track and an image capture module. The feeding container is used for accommodating the objects to be tested, the track conveying device is connected to the feeding container for conveying the objects to be tested, and the transparent track is separated with the track conveying device to further convey the objects to be tested. In addition, the image capture module is located adjacent to the track conveying device and the transparent track to capture images of the objects to be tested to judge the quality of the objects to be tested. In addition, the image capture module includes a plurality of image sensors, and a plurality of lighting devices to illuminate the objects to be tested while passing through the transparent track.

13 Claims, 8 Drawing Sheets

(56)                    References Cited

U.S. PATENT DOCUMENTS

| | | | | |
|---|---|---|---|---|
| 2019/0174119 | A1* | 6/2019 | Peeters | G06T 7/0004 |
| 2020/0193587 | A1* | 6/2020 | Mairhofer | G06T 7/0004 |
| 2020/0410662 | A1* | 12/2020 | Jha | G01N 21/8806 |
| 2021/0158505 | A1* | 5/2021 | Beppu | G01N 21/909 |
| 2021/0358120 | A1* | 11/2021 | Nomura | G06T 7/62 |
| 2022/0291148 | A1* | 9/2022 | Gill | G01N 33/02 |
| 2022/0390383 | A1* | 12/2022 | Sakane | G03B 33/08 |
| 2023/0247312 | A1* | 8/2023 | Ishida | G01N 21/8851 |
| | | | | 348/92 |
| 2023/0288349 | A1* | 9/2023 | Tsuchiya | G01N 21/90 |
| 2024/0024922 | A1 | 1/2024 | Kim et al. | |
| 2024/0046613 | A1* | 2/2024 | Miyamoto | B07C 5/3425 |
| 2024/0201085 | A1* | 6/2024 | Nagashima | G01N 21/8806 |

FOREIGN PATENT DOCUMENTS

| | | |
|---|---|---|
| TW | M623910 U | 3/2022 |
| WO | 2022/050579 A1 | 3/2022 |

* cited by examiner

AUTOMATIC FOOD INSPECTION DEVICE

RELATED APPLICATIONS

This application claims priority to Taiwan Application Serial Number 111144059, filed Nov. 17, 2022, the disclosures of which are incorporated herein by reference in their entireties.

TECHNICAL FIELD

The present disclosure relates to a food inspection device. More particularly, the present disclosure relates to an automatic food inspection device.

BACKGROUND

With the increasing progress of society, the quality of people life is also improving day by day. With the improvement of modern people's living conditions, tasting high-quality food has become an important part of life. Taking coffee as an example, coffee has become a very important beverage in modern people's daily lives. The unique coffee flavor depends on the selection of coffee beans and the roasting technology of the barista. Different temperatures and roasting times may bring different tastes to the coffee. The quality of the coffee is starting from the selection of coffee beans, and a traditional method of selecting coffee beans is manual selection to remove defects in the coffee beans.

With the increasing advancement of science and technology, machines are used to screen defective products such as beans, such as coffee beans, or grains, and are also widely used in large food factories or businesses. However, for specialty coffee lovers and small quantities of roasted coffee demanders, there is a need to be able to provide a convenient and accurate screening device for beans, such as coffee beans, or grains.

SUMMARY

The summary of the present invention is intended to provide a simplified description of the disclosure to enable readers to have a basic understanding of the disclosure. The summary of the present invention is not a complete overview of the disclosure, and it is not intended to point out the importance of the embodiments/key elements of the present invention or define the scope of the invention.

One objective of the embodiments of the present invention is to provide an automatic food inspection device able to be conveniently screen beans, such as coffee beans, or grains.

To achieve these and other advantages and in accordance with the objective of the embodiments of the present invention, as the embodiment broadly describes herein, the embodiments of the present invention provides an automatic food inspection device including a feeding container, a track conveying device, a transparent track and an image capture module. The feeding container accommodates objects to be tested, the track conveying device is connected to the feeding container to deliver the objects to be tested, the transparent track is separated with the track conveying device to further deliver the objects to be tested and the image capture module is located adjacent to the track conveying device and the transparent track to capture images of the objects to be tested to judge qualities of the objects to be tested. In addition, the image capture module includes a plurality of image sensors and a plurality of lighting devices. The image sensors are arranged on both sides of the transparent track and opposite to each other and the lighting devices are also arranged on the both sides of the transparent track to illuminate the transparent track so as to illuminate the objects to be tested passing through the transparent track.

In some embodiments, the transparent track is a transparent tempered glass track at an angle between 45 degrees and 75 degrees to a horizontal plane.

In some embodiments, the lighting devices surround the image sensors.

In some embodiments, each of the image sensors is equipped with 4 lighting devices surrounded the each of the image sensors.

In some embodiments, the lighting devices are located outside a detection area of the image sensors.

In some embodiments, the image capture module further includes a plurality of light absorbing devices surrounding the image sensors to absorb a light from the lighting devices.

In some embodiments, the automatic food inspection device further includes an analysis control module and a screening module. The analysis control module may judge qualities of the objects to be tested according to the images of the objects to be tested and the screening module connected to the image capture module may classify the objects to be tested according to judgment results of the analysis control module.

In some embodiments, the screening module includes a plurality of detectors and a plurality of air nozzles. The detectors may detect the objects to be tested while passing through and the air nozzles may change the moving paths of the objects to be tested when the objects to be tested are detected by the detectors and the analysis control module determines the qualities of the objects to be tested are defective.

In some embodiments, the screening module further includes a classification box having a partition, a first storage tank and a second storage tank, and the partition is located between the first storage tank and the second storage tank.

In some embodiments, the detectors include a plurality of infrared sensors to detect the objects to be tested while passing through.

According to another aspect, the present invention provides an automatic food inspection device including a feeding container, a track conveying device, an analysis control module and a screening module. The feeding container accommodates objects to be tested. The track conveying device is connected to the feeding container, and the track conveying device includes a conveying track and a vibrator. The conveying track has a first end and a second end, the vibrator is connected to the first end of the conveying track to drive the objects to be tested to move forward to the second end. The analysis control module judges qualities of the objects to be tested, and the screening module classifies the objects to be tested according to judgment results of the analysis control module.

In some embodiments, the conveying track includes a U-shaped track.

In some embodiments, the automatic food inspection device further includes a propulsion device installed below the feeding container to push the objects to be tested entering into the first end of the conveying track.

In some embodiments, the propulsion device includes at least one pneumatic cylinder, and at least one pneumatic cylinder push rod of the at least one pneumatic cylinder is aligned with at least one U-shaped track.

In some embodiments, the automatic food inspection device further includes a feeding guide chute installed below the feeding container to accommodate the objects to be tested, and the at least one pneumatic cylinder push rod of the at least one pneumatic cylinder pushes the objects to be tested in the feeding guide chute into the at least one U-shaped track of the conveying track.

In some embodiments, the automatic food inspection device further includes an inlet stopper installed at one end of the feeding guide chute, the inlet stopper including at least one opening respectively aligned with the at least one U-shaped track to ensure the objects to be tested being pushed into the at least one U-shaped track.

In some embodiments, the track conveying device further includes an anti-shooting baffle disposed above the conveying track to prevent the objects to be tested shooting from the conveying track.

In some embodiments, the at least one U-shaped track includes a first U-shaped track and a second U-shaped track, and the second U-shaped track is parallel with the first U-shaped track to deliver the objects to be tested with the first U-shaped track and the second U-shaped track.

In some embodiments, the first U-shaped track and the second U-shaped track respectively include a first retaining wall, a second retaining wall, a horizontal base plate, a first connecting arc and a second connecting arc. The second retaining wall is disposed opposite to the first retaining wall, the first connecting arc is connected between the first retaining wall and the horizontal base plate, and the second connecting arc is connected between the second retaining wall and the horizontal base plate. In addition, the horizontal base plate includes a width smaller than a maximum diameter of the objects to be tested, and a width between the first retaining wall and the second retaining wall is greater than 2-3 times the maximum diameter of the objects to be tested.

In some embodiments, the vibrator includes a linear vibrator and a vibration direction of the linear vibrator is parallel to a conveying direction of the conveying track.

Hence, the automatic food inspection device not only has a compact size and can be conveniently moved by the user with both hands, but also uses a propulsion device to prevent the objects to be tested, e.g. coffee beans, from accumulating on the entrance of the conveying track. One side of the U-shaped track fixed to the linear vibrator may improve the arrangement and advancement of the objects to be tested, e.g. coffee beans. The transparent tempered glass may reduce the number of rotations of the objects to be tested, e.g. coffee beans, and slow down the falling speed so as to provide the image and the configuration of the light-emitting diode light source from two sides and increase the clarity of the image. The configuration of infrared detectors and nozzles may more accurately classify the objects to be tested, e.g. coffee beans, and improve the classification quality and accuracy of the objects to be tested, e.g. coffee beans.

BRIEF DESCRIPTION OF THE DRAWINGS

The disclosure can be more fully understood by reading the following detailed description of the embodiment, with reference made to the accompanying drawings as follows.

4

Figure 2:
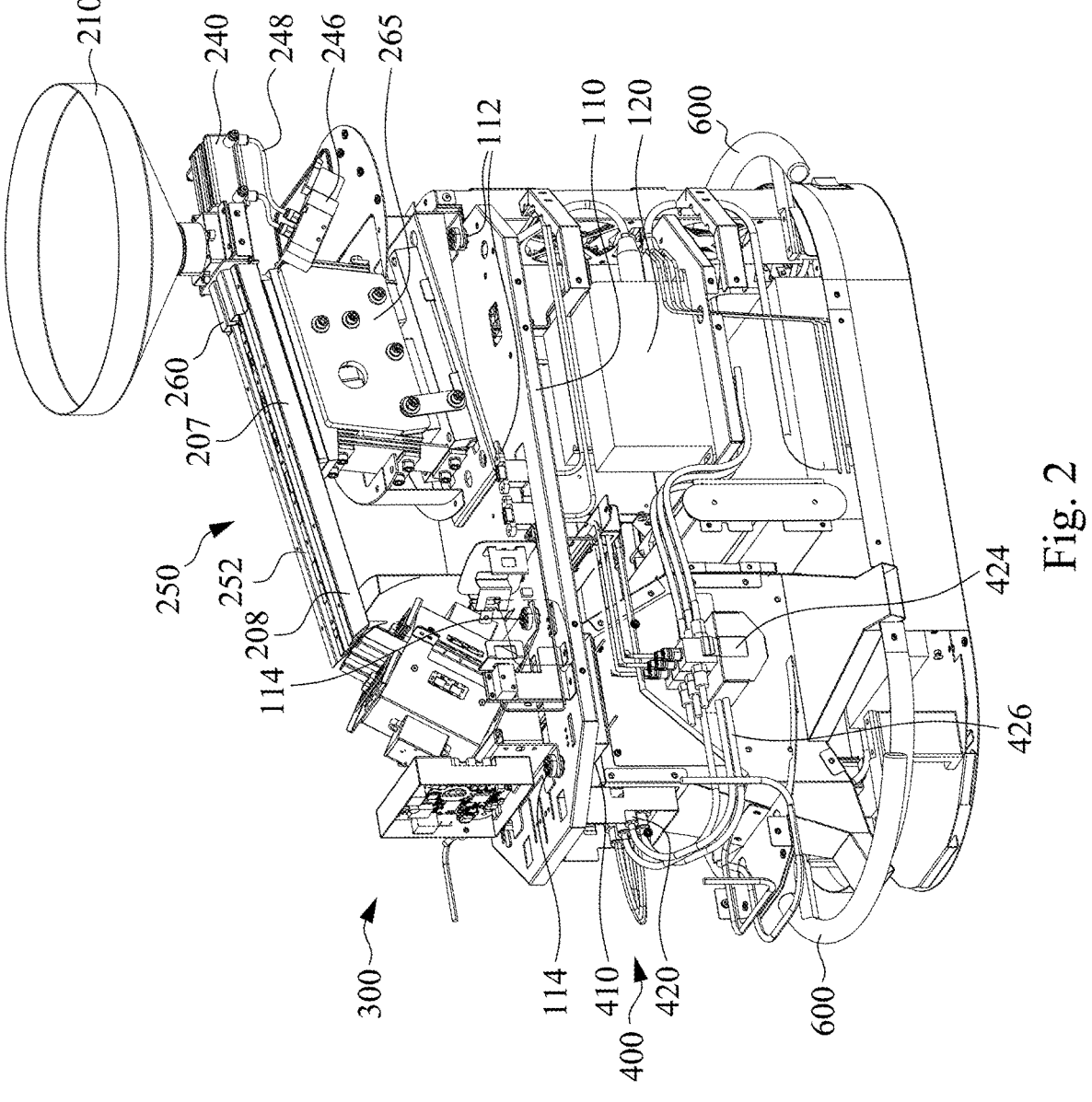
Figure 3:
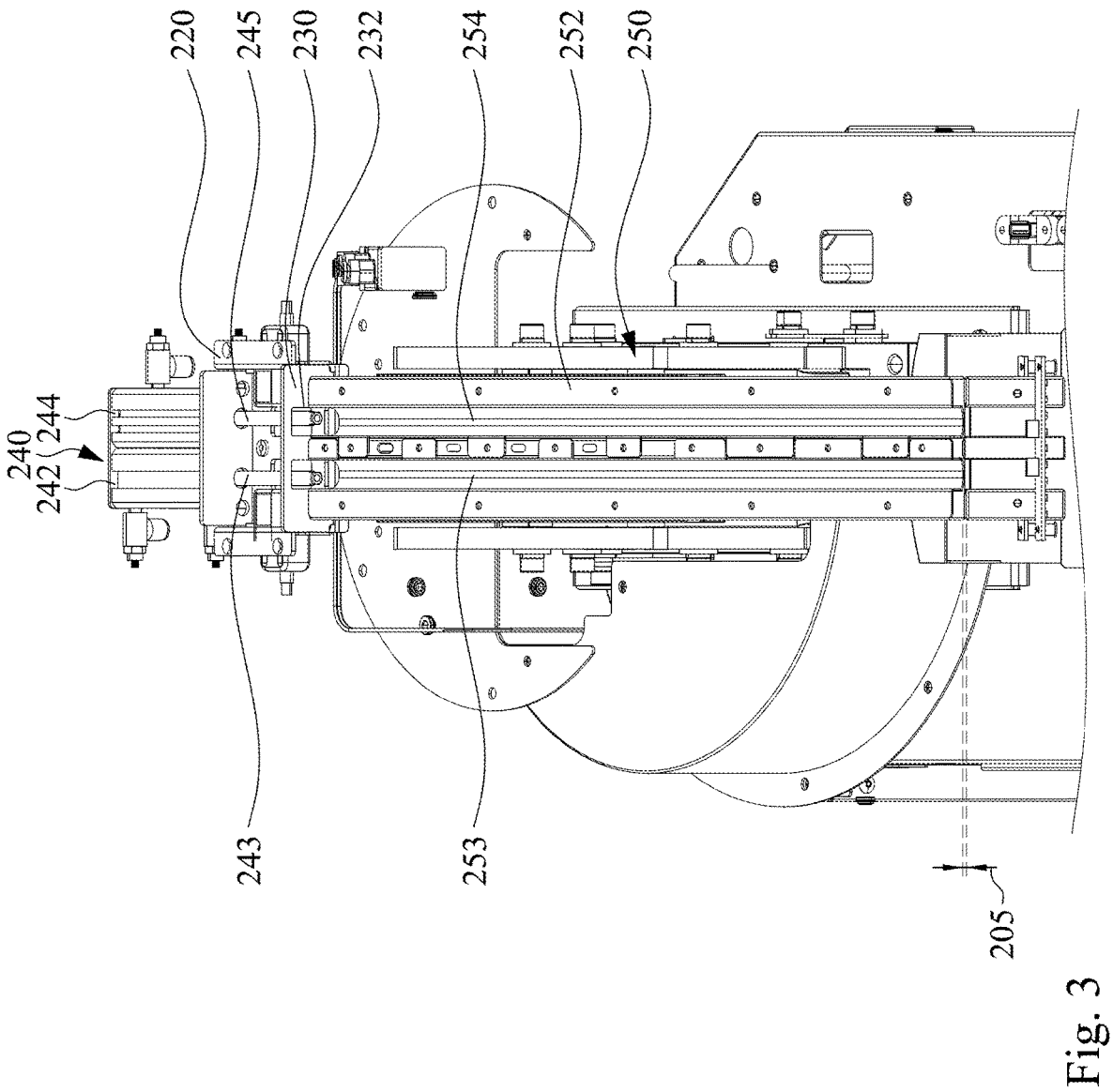
Figure 4:
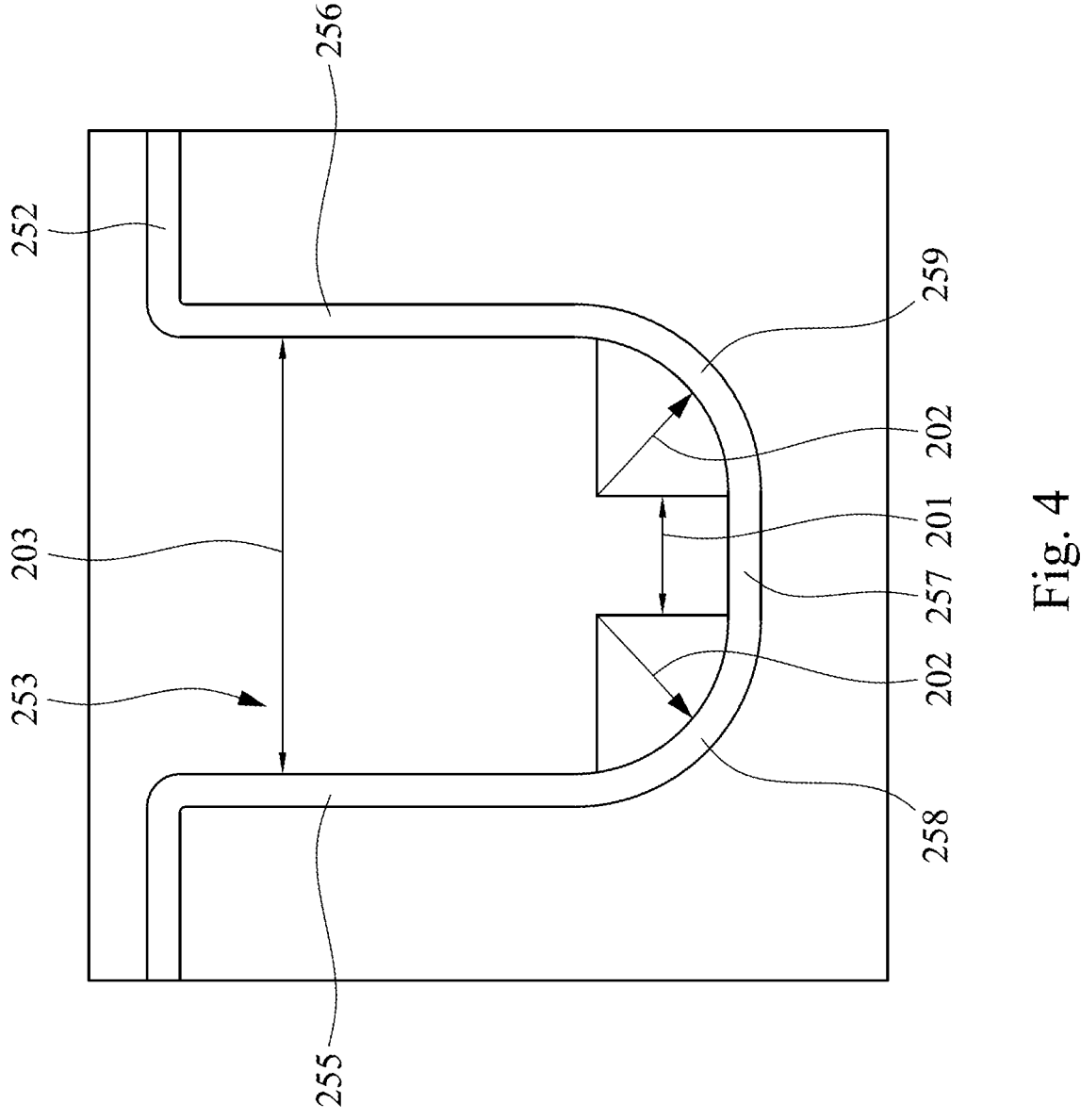
Figure 5:
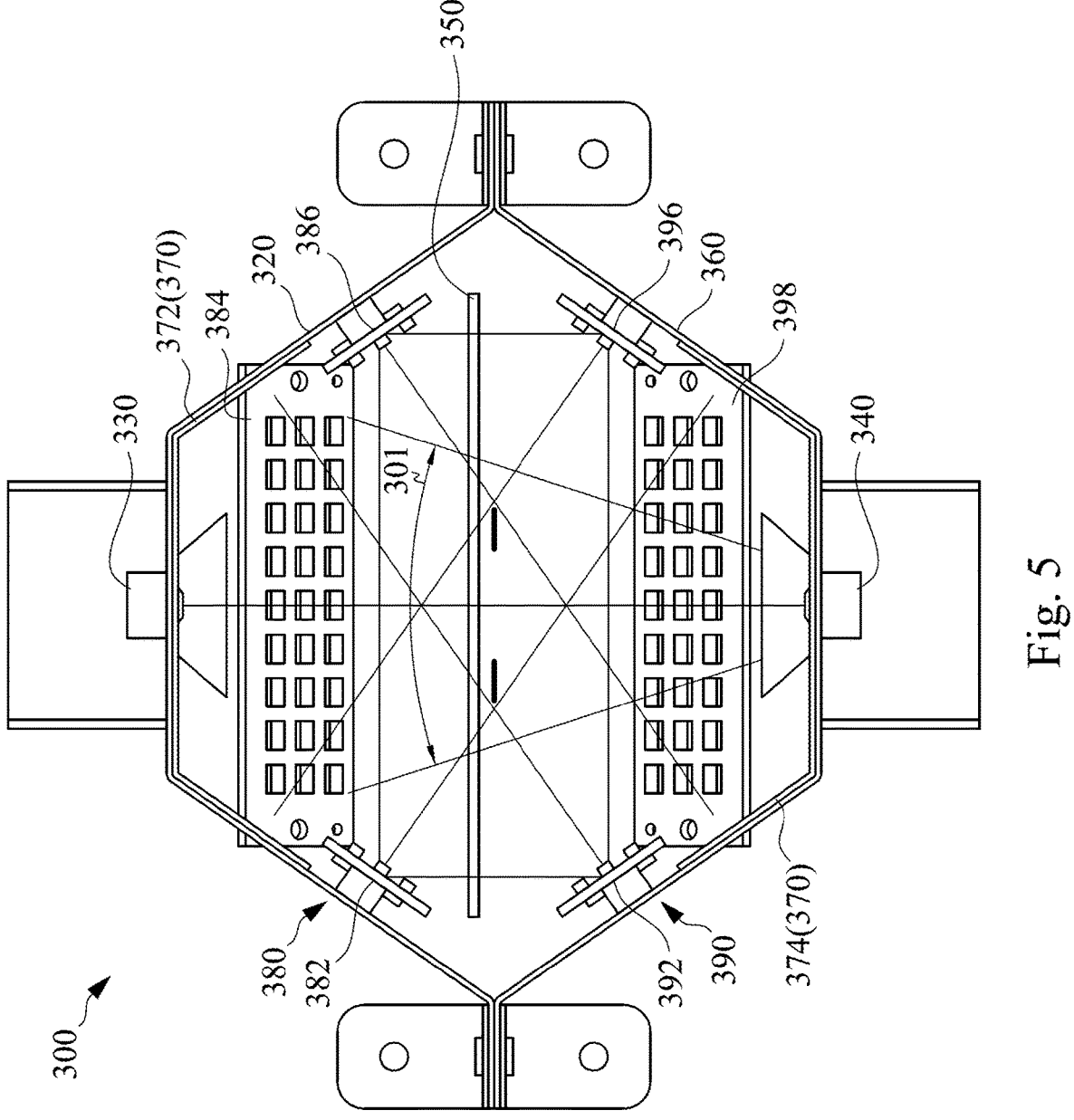
Figure 6:
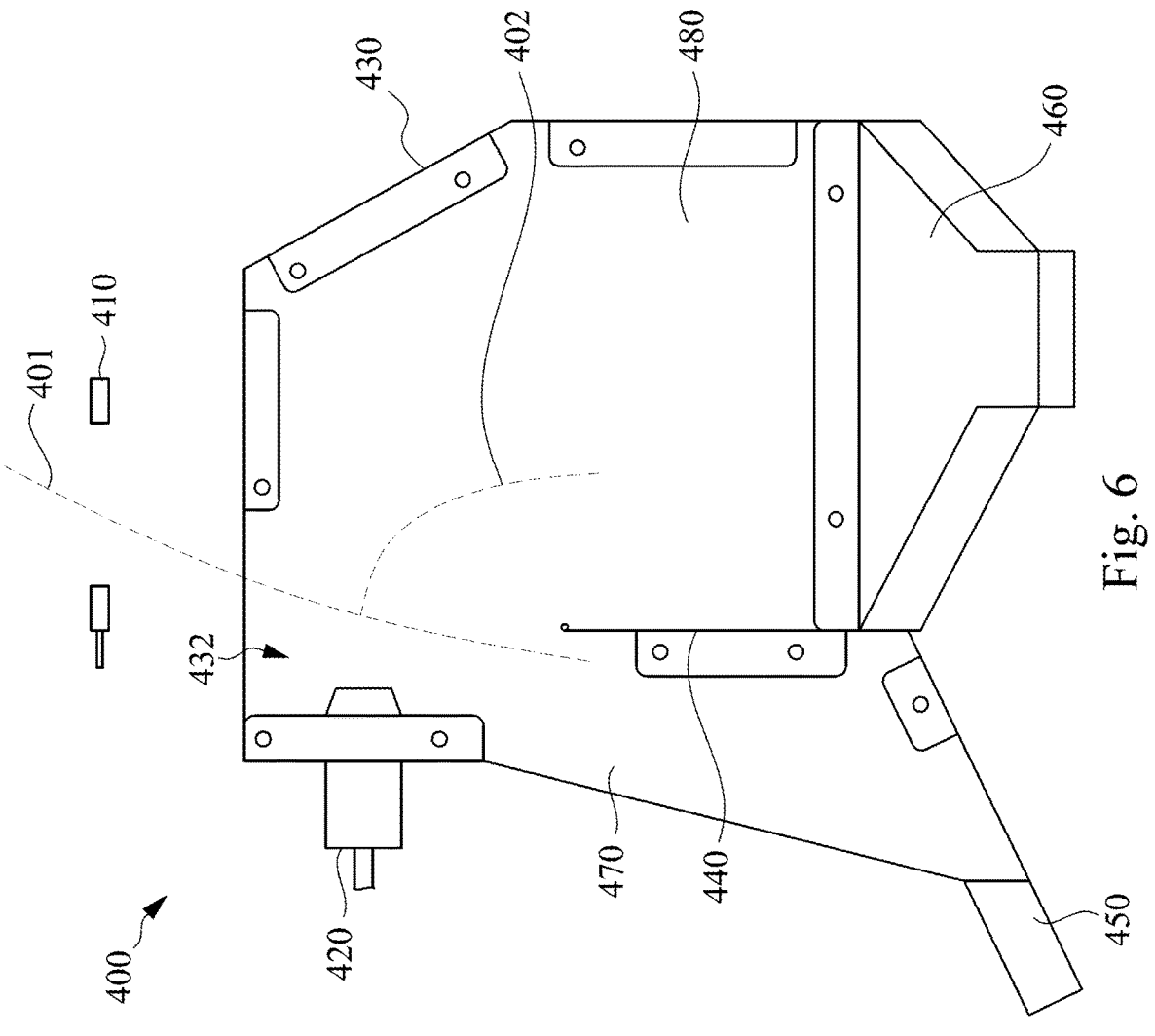
Figure 7:
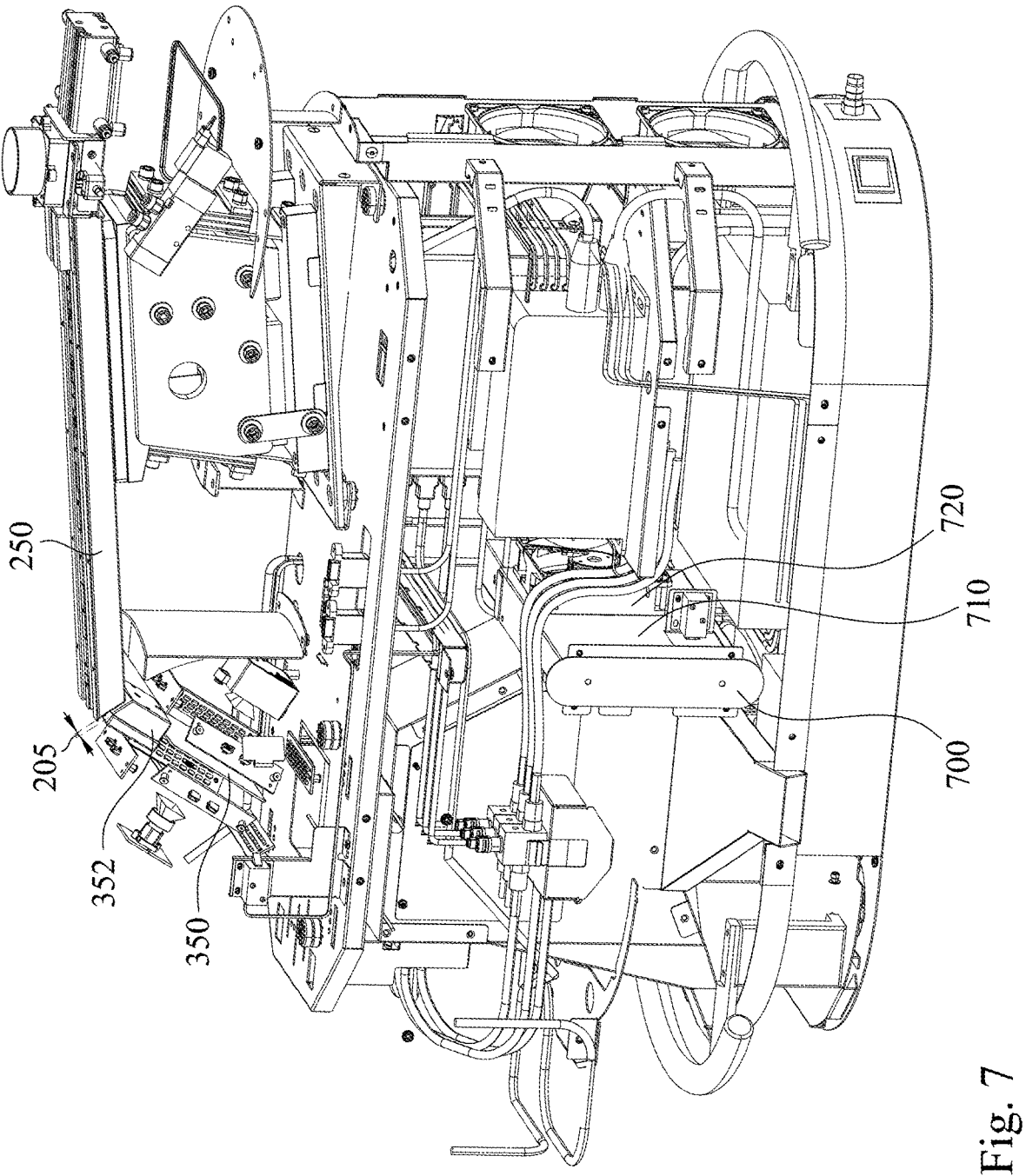
Figure 8:
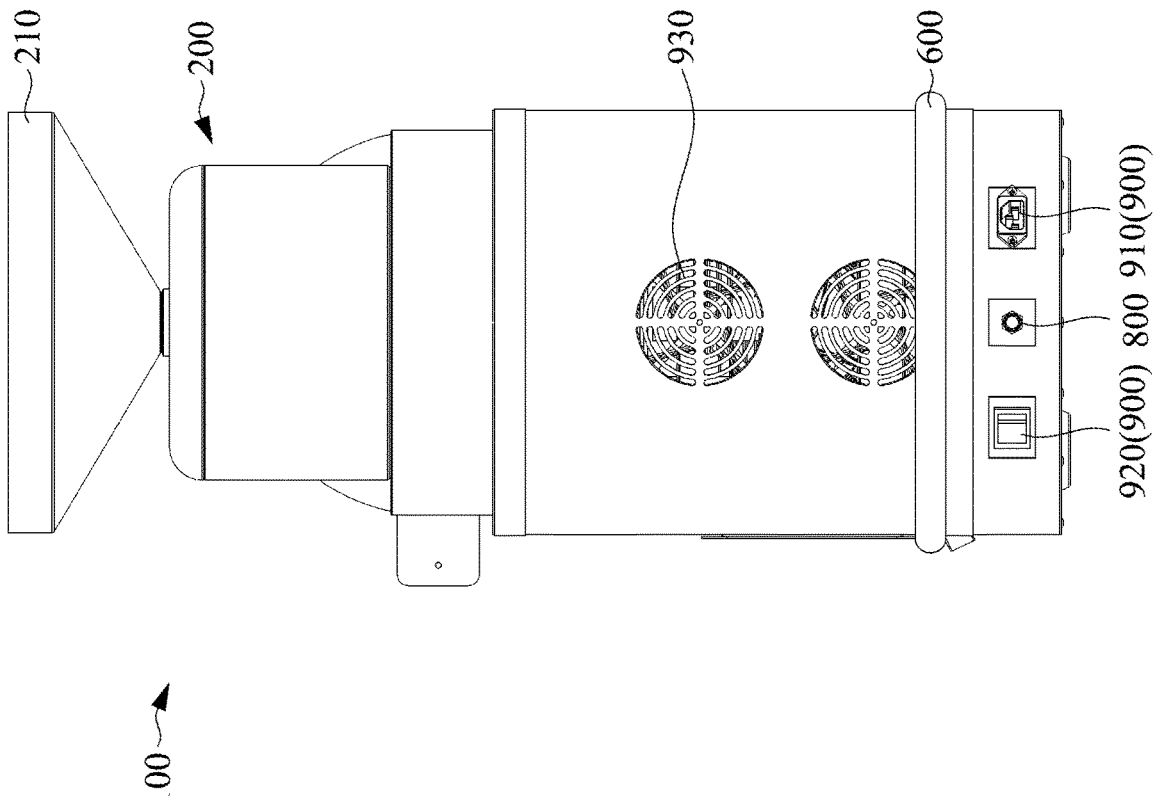

FIG. 2 illustrates a schematic perspective diagram showing an automatic food inspection device according to one embodiment of the present invention after the shells thereof are removed;

FIG. 3 illustrates a schematic diagram showing partial components of a feeding module of an automatic food inspection device according to one embodiment of the present invention;

FIG. 4 illustrates a schematic enlarged diagram showing a U-shaped track of a feeding module of an automatic food inspection device according to one embodiment of the present invention;

FIG. 5 illustrates a schematic diagram showing partial components of an image capture module of an automatic food inspection device according to one embodiment of the present invention;

FIG. 6 illustrates a schematic diagram showing partial components of a screening module of an automatic food inspection device according to one embodiment of the present invention;

FIG. 7 illustrates a schematic diagram showing a dust collection device of an automatic food inspection device according to one embodiment of the present invention; and FIG. 8 illustrates a schematic perspective diagram showing an automatic food inspection device according to one embodiment of the present invention from another view angle.

DETAILED DESCRIPTION OF THE PREFERRED EMBODIMENT

The following is a detailed description of the embodiments in conjunction with the accompanying drawings, but the provided embodiments are not intended to limit the scope of the disclosure, and the description of the structure and operation is not used to limit the execution sequence thereof. The structure of the recombination of components and the resulting devices with equal functions are all within the scope of this disclosure. In addition, the drawings are for illustration purposes only, and are not drawn according to the original scale. For ease of understanding, the same reference numbers are used in the drawings and the description to refer to the same or like parts.

In addition, the terms used in the entire description and the scope of the patent application, unless otherwise specified, usually have the usual meaning of each term used in this field, in the content disclosed here and in the special content. Some terms used to describe the disclosure are discussed below or elsewhere in this specification to provide additional guidance to those skilled in the art in the disclosure.

In the implementation mode and the scope of the present application, unless the article is specifically limited in the context, "a" and "the" can generally refer to a single or pluralities. In the steps, the numbering is only used to conveniently describe the steps, rather than to limit the sequence and implementation.

Secondly, the words "comprising", "including", "having", "containing" and the like used in the present application are all open language, meaning including but not limited to.

Figure 1:
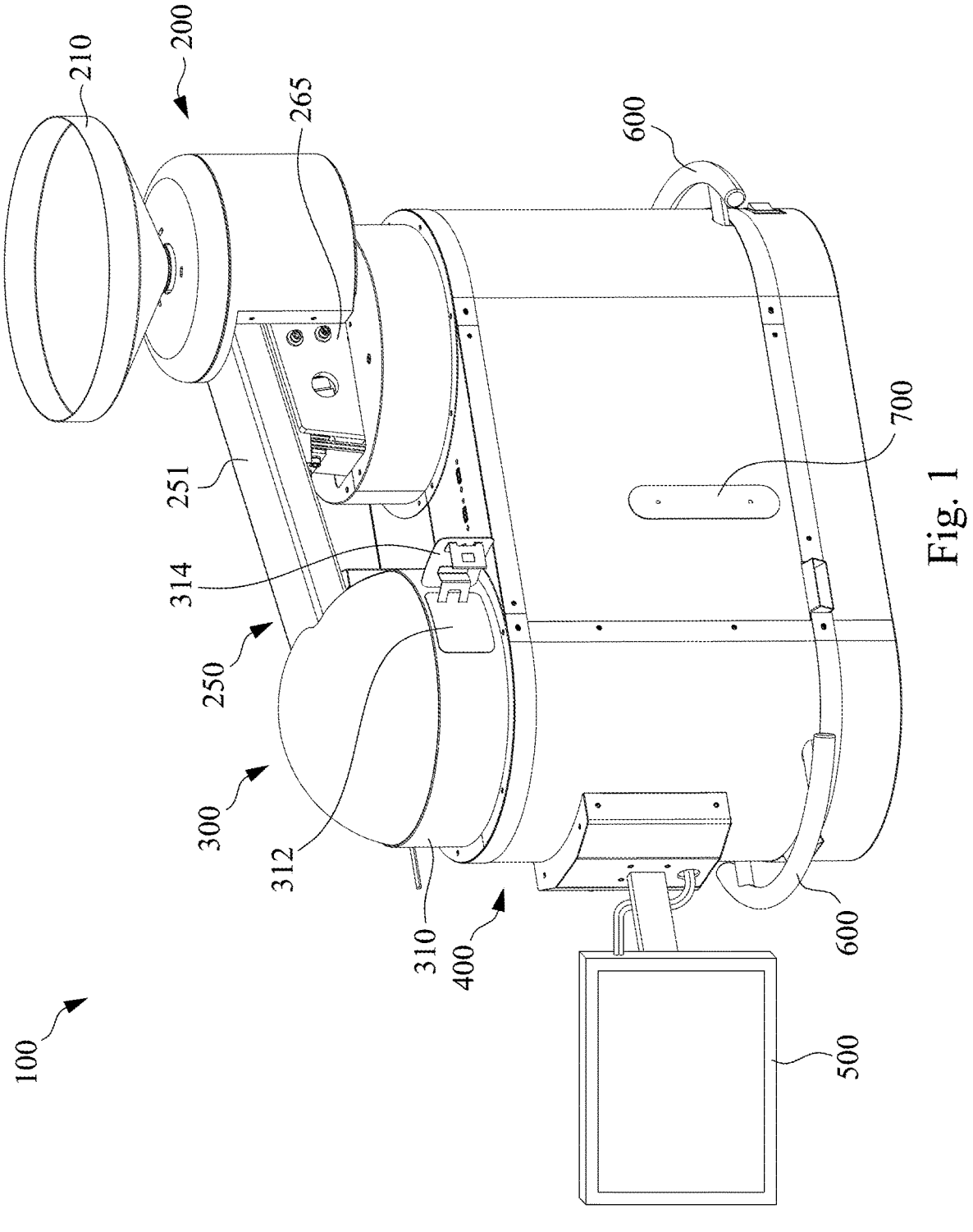
FIG. 1 illustrates a schematic perspective diagram showing an automatic food inspection device according to one embodiment of the present invention.

FIG. 1 illustrates a schematic perspective diagram showing an automatic food inspection device according to one embodiment of the present invention, FIG. 2 illustrates a schematic perspective diagram showing the automatic food inspection device after the shells thereof are removed, FIG. 3 illustrates a schematic diagram showing partial components of a feeding module of the automatic food inspection device, FIG. 4 illustrates a schematic enlarged diagram showing a U-shaped track of a feeding module of the automatic food inspection device, FIG. 5 illustrates a schematic diagram showing partial components of an image capture module of the automatic food inspection device, FIG. 6 illustrates a schematic diagram showing partial components of a screening module of the automatic food inspection device, FIG. 7 illustrates a schematic diagram showing a dust collection device of the automatic food inspection device and FIG. 8 illustrates a schematic perspective diagram showing the automatic food inspection device from another view angle.

First referring to FIG. 1 and FIG. 2, the automatic food inspection device 100 includes a feeding module 200, an image capture module 300, a screening module 400, an operation display panel 500, handles 600 and a dust collection device 700. In some embodiments, the automatic food inspection device may screen food through image analysis to screen out high-quality food. Image analysis may, for example, use the color, size, outline and other parameters of the food image as a basis for screening. In some embodiments, the food may be, for example, coffee beans, any other beans or grains. In some embodiments, the automatic food inspection device may be a coffee screening machine.

In addition, the feeding module 200 includes a feeding container 210, a track conveying device 250, a vibrator 265 and a propulsion device 240.

The feeding container 210 is used for accommodating the objects to be tested, for example, beans, such as coffee beans, or grains. The track conveying device 250 is connected to the feeding container 210 to convey the objects to be tested to the image capture module 300.

In addition, the track conveying device 250 includes a conveying track 252 and a vibrator 265. The conveying track 252 includes a first end 207 and a second end 208, the first end 207 is connected to one side of the feeding container 210, and the second end 208 is located adjacent to the image capture module 300. The vibrator 265 is connected to the first end 207 of the conveying track 252 to drive the objects to be tested to move forward to the second end 208. In addition, since the conveying track 252 is a cantilever beam and fixed on the vibrator 265, some objects to be tested stacked on the second end 208 of the conveying track 252 may be separated from each other due to the swing of the conveying track 252 caused by the elastic deformation of the conveying track 252 when the vibrator 265 vibrates. Therefore, the objects to be tested, i.e. coffee beans, may move forward sequentially along the conveying track 252 and are separated from each other.

The image capture module 300 is located adjacent to the second end 208 of the conveying track 252 to capture images of the objects to be tested to judge the quality of the objects to be tested, for example, to judge the difference of the objects to be tested. In some embodiments, the quality of coffee beans, other beans, or grains can then be determined by capturing images thereof. In addition, the detailed descriptions of each component will be exemplified in subsequent paragraphs. Furthermore, the screening module 400 is disposed below the image capture module 300 to classify the objects to be tested according to the judgment results of the analysis control module.

In addition, the propulsion device 240 is installed below the feeding container 210 to push the objects to be tested into the first end 207 of the conveying track 252. In some embodiments, the propulsion device 240 includes a first control valve 246 to deliver the high pressure air to the propulsion device 240 by way of the high pressure pipe 248 so as to control the movement of the pneumatic cylinder push rod of the propulsion device 240 to effectively push the objects to be tested into the first end 207 of the conveying track 252.

In some embodiments, the image capture module 300 includes a protective shell 310, and the protective shell 310 includes a cleaning opening 312 to conveniently clean the image capture module 300 by users to improve the accuracy and efficiency of image detection. In addition, an observation window 314 is further equipped on the cleaning opening 312, and the observation window 314 preferably includes at least part transparent observation window to allow the users observing the cleanliness of the components of the image capture module 300 from the outside to avoid internal contamination caused by long-term use.

Simultaneously referring to FIG. 3, the conveying track 252 includes at least one U-shaped track. In some embodiments, the conveying track 252 may include a plurality of U-shaped tracks, for example, a first U-shaped track 253 and a second U-shaped track 254, but not limited thereto. The conveying track 252 may include one, two or more U-shaped tracks to individually or simultaneously transport and inspect a plurality of objects to be tested without departing from the spirit and scope of the disclosure.

In some embodiments, the first U-shaped track 253 and the second U-shaped track 254 are disposed in parallel to simultaneously transport the objects to be tested through the first U-shaped track 253 and the second U-shaped track 254.

In some embodiments, the propulsion device 240 of the feeding module 200 of the automatic food inspection device 100 includes a first pneumatic cylinder 242 and a second pneumatic cylinder 244, and a first pneumatic cylinder push rod 243 of the first pneumatic cylinder 242 is aligned with the first U-shaped track 253, and a second pneumatic cylinder push rod 245 of the second pneumatic cylinder 244 is aligned with the second U-shaped track 254.

In some embodiments, the feeding module 200 of the automatic food inspection device 100 includes a feeding guide chute 220 installed below the feeding container 210 to accommodate the objects to be tested falling from the feeding container 210, and the first pneumatic cylinder push rod 243 of the first pneumatic cylinder 242 and the second pneumatic cylinder push rod 245 of the second pneumatic cylinder 244 further push the objects to be tested in the feeding guide chute 220 into the first U-shaped track 253 and the second U-shaped track 254 of the conveying track 252.

In some embodiments, the feeding module 200 of the automatic food inspection device 100 further includes an inlet stopper 230 equipped on one side of the feeding guide chute 220. The inlet stopper 230 includes a plurality of openings 232 respectively aligned with the first U-shaped track 253 and the second U-shaped track 254 to ensure that the objects to be tested are pushed into the first U-shaped track 253 and the second U-shaped track 254 rather than falling into the interior of the automatic food inspection device 100. In addition, the width of the opening 232 is preferably greater than 2-3 times the diameter of the objects to be tested, for example, the width of the opening 232 is greater than 10 mm and preferably greater than 16 mm while the diameter of the coffee beans is about 5-8 mm.

In some embodiments, the feeding module 200 of the automatic food inspection device 100 further includes an anti-shooting baffle 260 disposed above the conveying track 252 to prevent the object to be tested from being ejected from the conveying track 252.

In some embodiments, the feeding module 200 of the automatic food inspection device 100 further includes a protective cover 251 covering the conveying track 252 and the anti-shooting baffle 260 to prevent the objects to be tested from being contaminated, and the protective cover 251 may also prevent the objects to be tested from spilling from the conveying track 252 or falling into the interior of the automatic food inspection device 100.

Further referring to FIG. 4, the first U-shaped track 253 is illustrated as an example, and the second U-shaped track 254 and the first U-shaped track 253 have the same appearance.

The first U-shaped track 253 includes a first retaining wall 255, a second retaining wall 256, a horizontal base plate 257, a first connecting arc 258 and a second connecting arc 259. The first retaining wall 255 is arranged opposite the second retaining wall 256, and the horizontal base plate 257 is arranged below.

The first retaining wall 255, the second retaining wall 256 and the horizontal base plate 257 are generally flat plates, but not limited thereto. In addition, the first connecting arc 258 is connected between the first retaining wall 255 and the horizontal base plate 257, the second connecting arc 259 is connected between the second retaining wall 256 and the horizontal base plate 257. The horizontal base plate 257 has a width 201, preferably smaller than a maximum diameter of the objects to be tested. In some embodiments, taking the coffee bean as an example, the width 201 is preferably smaller than 5 mm, such as 4 mm or more preferably 3 mm, while the maximum diameter of the coffee beans is about 5-8 mm.

In some embodiments, a width 203 between the first retaining wall 255 and the second retaining wall 256 is greater than 2-3 times the maximum diameter of the objects to be tested. In some embodiments, taking the coffee bean as an example, the width 203 is greater than 10 mm and preferably 16 mm, while the maximum diameter of the coffee beans is about 5-8 mm.

In some embodiments, the width 203 between the first retaining wall 255 and the second retaining wall 256 is preferably greater than a width of the opening 232 of the inlet stopper 230 to ensure the coffee beans passed through the opening 232 of the inlet stopper 230 may further enter into the first U-shaped track 253 or the second U-shaped track 254 to prevent the coffee beans stuck at the entrance of the first U-shaped track 253 and the second U-shaped track 254.

In some embodiments, the radius 202 of the first connecting arc 258 and the second connecting arc 259 is smaller than the maximum diameter of the objects to be tested. In some embodiments, taking the coffee bean as an example, the radius 202 is preferably smaller than 5 mm, such as 4.5 mm, while the maximum diameter of the coffee beans is about 5-8 mm.

Therefore, when the coffee beans are transported in the first U-shaped track 253 and the second U-shaped track 254, since the horizontal base plate 257 is a flat plate having a width 201 smaller than the maximum diameter of the coffee beans, the coffee bean may not lie flat on the horizontal base plate 257, and one end of the coffee bean may contact the first connecting arc 258 or the second connecting arc 259 so that the first connecting arc 258 and the second connecting arc 259 may generate a thrust toward the center of the U-shaped track on the coffee beans to force the coffee beans respectively aligning to the center of the first U-shaped track 253 and the second U-shaped track 254, thereby making the coffee beans dispersedly arranged and continuously advanced in the first U-shaped track 253 and the second U-shaped track 254 and further reducing the situation of coffee beans stacking or moving sideways in the first U-shaped track 253 and the second U-shaped track 254.

In some embodiments, the track conveying device 250 further includes a plurality of shock-absorbing feet 112 to fix the vibrator 265 on the supporting plate 110 so as to effectively isolate the vibration of the vibrator 265 and the supporting plate 110. Therefore, the other components of the automatic food inspection device 100 may not be affected by the vibration generated by the vibrator 265.

In some embodiments, the vibrator 265 is a linear vibrator, and the vibration direction of the linear vibrator is parallel to a conveying direction of the conveying track 252. That is to say, the linear vibrator vibrates along the first end 207 and the second end 208 of the conveying track 252 to effectively transport the objects to be tested downstream to the image capture module 300.

In some embodiments, the conveying track 252 has an angle of approximately 5-20 degrees, preferably 6-8 degrees, from the horizontal plane.

In addition, the feeding module 200 of the automatic food inspection device 100 may use the vibration of the vibrator 265 to gradually push the objects to be tested to the conveying track 252, and the first pneumatic cylinder push rod 243 of the first pneumatic cylinder 242 and the second pneumatic cylinder push rod 245 of the second pneumatic cylinder 244 may also push the coffee beans into the first U-shaped track 253 and the second U-shaped track 254 so as to improve the inspection efficiency of the coffee beans and reduce the failure or inspection efficiency reduction due to the coffee beans stuck at the entrance of the first U-shaped track 253 and the second U-shaped track 254.

Further referring to FIG. 5, the automatic food inspection device 100 may further includes a transparent track 350 equipped in the image capture module 300. The image capture module 300 includes a plurality of image sensors, for example, a first image sensor 330 and a second image sensor 340, a plurality of lighting devices, for example, a first lighting device 380 and a second lighting device 390.

The transparent track 350 and the track conveying device 250 are separated from each other to convey the objects to be tested. The transparent track 350 is separated from the track conveying device 250 by at least a gap 205. Therefore, the vibration of the track conveying device 250 may not affect the transparent track 350, and may not further affect the first image sensor 330, the second image sensor 340, the first lighting devices 380 and the second lighting devices 390 so as to improve the accuracy and safety for capturing images and further improve the service life of the automatic food inspection device 100.

Simultaneously referring to FIG. 7, in some embodiments, the transparent track 350 further includes a clamping device 352 to clamp the transparent track 350, and the track conveying device 250 is separated from the clamping device 352 of the transparent track 350 by at least a gap 205. Therefore, the vibration of the track conveying device 250 may not affect the transparent track 350 and the clamping device 352, and may not further affect the first image sensor 330, the second image sensor 340, the first lighting devices 380 and the second lighting devices 390 so as to improve the accuracy and safety for capturing images and further improve the service life of the automatic food inspection device 100.

The first image sensor 330 and the second image sensor 340 are preferably arranged on both sides of the transparent track 350 and opposite to each other, and the first lighting devices 380 and the second lighting devices 390 are also arranged on both sides of the transparent track 350 to illuminate the objects to be tested on the transparent track 350.

In some embodiments, the first lighting devices 380 includes a first LED light 382, a second LED light 384, a third LED light 386 and a fourth LED light (not shown), and the first LED light 382, the second LED light 384, the third LED light 386 and the fourth LED light are arranged beside the first image sensor 330 to illuminate the objects to be tested located at a detection area of the first image sensor 330 to increase the brightness of the surfaces of the objects to be tested so as to increase the image clarity and further improve the accuracy and efficiency of quality judgements of the objects to be tested. In some embodiments, the first LED light 382, the second LED light 384, the third LED light 386 and the fourth LED light may surround the first image sensor 330.

In some embodiments, the second lighting device 390 include a first LED light 392, a second LED light (not shown), a third LED light 396 and a fourth LED light 398 are arranged beside the second image sensor 340 to illuminate the objects to be tested located at a detection area of the first image sensor 330 to increase the brightness of the surfaces of the objects to be tested so as to increase the image clarity and further improve the accuracy and efficiency of quality judgements of the objects to be tested. In some embodiments, the first LED light 392, the second LED light (not shown), the third LED light 396 and the fourth LED light 398 may surround the second image sensor 340.

In some embodiments, the first image sensor 330 and/or the second image sensor 340 are, for example, charge coupled devices (CCD) or complementary metal-oxide semiconductors (CMOS), but not limited thereto. The first image sensor 330 and the second image sensor 340 are devices to convert optical signals of the objects to be tested into analog electrical signals, and then perform analog/digital conversion and color adjustment to become digital image information of the objects to be tested without departing from the spirit and scope of the disclosure.

The foregoing digital image information of the objects to be tested may further send to the analysis control module 120 to judge the quality of the objects to be tested according to the image information of the objects to be tested captured by the image sensors.

In some embodiments, the analysis control module 120 may receive or preload the classification information of quality of the objects to be tested to determine the quality of the objects to be tested while passing through the transparent track 350 by using the first image sensor 330 and/or the second image sensor 340 to capture front and back images of the objects to be tested and send to the analysis control module 120 for classifying the objects to be tested without departing from the spirit and scope of the disclosure.

In some embodiments, the analysis control module 120 may also perform self-learning, using artificial intelligence (AI) to learn, solve and identify the quality of the objects to be tested, such as coffee beans. In some embodiments, users may first put the defective coffee beans into the feeding module 200 of the automatic food inspection device 100, and then the images of defective coffee beans are captured by the image capture module 300 and the analysis control module 120 may identify defective coffee beans through learning and judgment. In addition, users may also put good coffee beans into the feeding module 200 of the automatic food inspection device 100, and then the images of good coffee beans are captured by the image capture module 300, and the analysis control module 120 identifies the images of good coffee beans through learning and judgment, and then the automatic food inspection device 100 may use them for subsequently judging the quality of coffee beans.

In some embodiments, the analysis control module 120 may connect to the network to determine good coffee beans and defective coffee beans using big data analysis. In addition, the automatic food inspection device 100 may also use big data analysis to determine the type of coffee beans currently being tested, and then further determine whether the coffee beans are good coffee beans according to big data information of this type coffee bean without departing from the spirit and scope of the disclosure.

In some embodiments, the analysis control module 120 may also be set up in the cloud or computer server, and the automatic food inspection device 100 may connect to the network and send the image of the objects to be tested captured by the image capture module 300 to the analysis control module 120 to determine the quality of the objects to be tested and the judgment results of the analysis control module may be sent back to the automatic food inspection device 100 to classify the subsequent objects to be tested.

In some embodiments, the transparent track 350 is a transparent tempered glass track, and aligned with a horizontal plane about an angle between 45 degrees and 75 degrees, preferably 60 degrees.

In some embodiments, the first LED light 382, the second LED light 384, the third LED light 386 and the fourth LED light of the first lighting devices 380 are respectively fixed on four internal surfaces of the first light shielding shell 320 to surround the first image sensor 330, and the first LED light 382, the second LED light 384, the third LED light 386 and the fourth LED light illuminate two objects to be tested transported in the first U-shaped track 253 and the second U-shaped track 254 of the transparent track 350 so as to simultaneously illuminate the surfaces of the two objects to be tested.

In some embodiments, the first LED light 392, the second LED light, the third LED light 396 and the fourth LED light 398 of the second lighting devices 390 are respectively fixed on four internal surfaces of the second light shielding shell 360 to surround the second image sensor 340, and the first LED light 392, the second LED light, the third LED light 396 and the fourth LED light 398 illuminate the back surfaces of two objects to be tested transported in the first U-shaped track 253 and the second U-shaped track 254 of the transparent track 350 so as to simultaneously illuminate another surfaces of the two objects to be tested.

In some embodiments, taking the detection area 301 of the second image sensor 340 as an example, the first LED light 382, the second LED light 384, the third LED light 386 and the fourth LED light of the first lighting devices 380 are respectively fixed on the shell of the first light shielding shell 320 and located outside the detection area 301 of the second image sensor 340 to prevent image quality reduction of the images of coffee beans captured by the second image sensor 340. In some embodiments, the detection area 301 of the second image sensor 340 is about 20-60 degrees, but not limited thereto. In some embodiments, the detection area 301 of the second image sensor 340 may preferably cover the two objects to be tested transported in the first U-shaped track 253 and the second U-shaped track 254 so as to simultaneously illuminate another surfaces of the two objects to be tested.

With the same manner, the detection area of the first image sensor 330 is about 20-60 degrees, but not limited thereto. In some embodiments, the detection area of the first image sensor 330 may preferably cover the two objects to be tested transported in the first U-shaped track 253 and the second U-shaped track 254 so as to simultaneously illuminate the surfaces of the two objects to be tested. In addition, the first LED light 392, the second LED light, the third LED light 396 and the fourth LED light 398 of the second lighting devices 390 are respectively fixed on the shell of the second light shielding shell 360 and located outside the detection area of the first image sensor 330 to prevent image quality reduction of the images of coffee beans captured by the first image sensor 330.

In some embodiments, the image capture module 300 further includes a plurality of light absorbing devices 370, for example, a first light absorbing pad 372 and a second light absorbing pad 374, respectively surrounding the first image sensor 330 and the second image sensor 340 and fitting on the internal surfaces of the first light shielding shell 320 and the second light shielding shell 360 to absorb the light generated by the first lighting devices 380 and the second lighting devices 390 to reduce the diffuse light in the first light shielding shell 320 and the second light shielding shell 360 so as to improve the image quality of the coffee beans captured by the first image sensor 330 and the second image sensor 340 and further improve the accuracy and efficiency of quality judgements of the objects to be tested.

Further referring to FIG. 6, after the analysis control module 120 determines the qualities of the objects to be tested, the objects to be tested may fall into the classification box 430 through the opening 432 of the classification box 430. For effectively classifying the good coffee beans and defective coffee beans, the screening module 400 includes a plurality of detectors 410, a plurality of air nozzles 420, a second control valve 424 and a high pressure pipe 426.

The high pressure pipe 426 is connected between the air nozzles 420 and the second control valve 424 to deliver the high pressure air from the high pressure pipe 426 to the air nozzles 420 through the second control valve 424 controlled by the analysis control module 120.

In addition, the detectors 410 and the air nozzles 420 are respectively aligned to the falling paths of the objects to be tested, and the detectors 410 is located above the air nozzles 420 along the falling paths of the objects to be tested. When the analysis control module 120 determines that the quality of the objects to be tested is defective, the air nozzle 420 located below the detector 410 may spray the high pressure air to change the moving paths of the objects to be tested.

In some embodiments, after the coffee beans fall from the transparent track 350, the coffee beans may fall along the coffee bean falling path 401 to move to the opening 432 of the classification box 430. The detector 410 may detect the coffee bean is passing through the coffee bean falling path 401 and the analysis control module 120 may determine whether the quality of the coffee bean is good. If the coffee beans are good, the coffee beans may continuously fall into the first storage tank 470 of the classification box 430 along the coffee bean falling path 401. If the coffee beans are defective, the coffee beans may be sprayed by the high pressure air from the air nozzles 420 to change the moving path thereof to fall into the second storage tank 480 of the classification box 430 along the bad coffee bean falling path 402. It is worth noting that the coffee bean from the first U-shaped track 253 and the coffee bean from the second U-shaped track 254 may use one image capture module 300 to determine the quality thereof. In addition, the two coffee beans are classified to store in the first storage tank 470 or the second storage tank 480 of the classification box 430 through respective detectors 410 and air nozzles 420.

In some embodiments, the detectors 410 may be infrared detectors, microwave detectors, radar detectors, light shielding detectors or any other detectors able to quickly detect the objects to be tested, without departing from the spirit and protection scope of the present invention.

In some embodiments, between the detectors 410 and the image capture module 300, a left coffee bean and a right coffee bean may pass through corresponding detectors 410 and be classified by corresponding air nozzles 420, without departing from the spirit and scope of the present invention.

In some embodiments, between the detectors 410 and the image capture module 300, a plurality of left coffee beans and a plurality of right coffee beans may continuously pass through corresponding detectors 410 and be counted by the detectors 410 to sequentially classify the coffee bean by air nozzles 420, but not limited thereto.

In some embodiments, the classification box 430 further includes a partition 440 located between the first storage tank 470 and the second storage tank 480 to respectively store the objects to be tested of different qualities, but not limited thereto. The classification box 430 may further include a third storage tank and/or a fourth storage tank for multi-level classification of beans such as coffee beans or grains, without departing from the spirit and scope of the present invention.

In some embodiments, the air pressure and the air velocity of the air nozzle 420 can be adjusted according to the number of the storage tanks and the height of the partition to blow the objects to be tested into the correct storage tank.

In some embodiments, the classification box 430 further includes a first exit 450 and a second exit 460, the first exit 450 is connected to the first storage tank 470, and the second exit 460 is connected to the second storage tank 480 to discharge the classified coffee beans through the first exit 450 and the second exit 460 to the external corresponding containers for subsequent processing.

In some embodiments, the image capture module 300 further includes a plurality of shock-absorbing feet 114 to fix the image capture module 300 on the supporting plate 110, so that the vibration of the vibrator 265 may be isolated to the image capture module 300 to effectively prevent from affecting the image capture module 300.

Referring to FIG. 7 again, the automatic food inspection device 100 further includes a dust collection device 700 to effectively filter out the dust inside the automatic food inspection device 100.

In some embodiments, the dust collection device 700 is preferably installed on one side of the classification box 430 to filter out the dust of the grains and beans such as coffee beans to prevent from contamination of the interior of the automatic food inspection device 100. In addition, the dust collection device 700 includes a dust collection filter 710 and a fan 720 to draw air from the classification box 430 by the fan 720 and then filter the air through the dust collection filter 710 to filter out the dust. In addition, the dust collection filter 710 can be removed from the dust collection device 700 to clean or replace the filter.

Referring to FIG. 8, the automatic food inspection device 100 further includes a pneumatic pressure input connector 800 to connect to an external air source to provide pressure air for the propulsion device 240 and the air nozzles 420 but the present invention is not limited to this. The automatic food inspection device 100 may further include a small air compressor without departing from the spirit and scope of the disclosure.

In addition, the automatic food inspection device 100 further includes a power module 900 having an alternating current (AC) connecter 910 and a switch 920, the AC connecter 910 is connected to a connector of a cable to input an external AC power but the present invention is not limited to this. The power module 900 of the automatic food inspection device 100 may also be a direct current (DC) power module or includes an internal battery without departing from the spirit and scope of the disclosure.

In some embodiments, the power module 900 of the automatic food inspection device 100 may further include a cooling fan 930 to effectively reduce the working temperature of the automatic food inspection device 100 so as to increase the working efficiency and working quality of the automatic food inspection device 100.

In some embodiments, the automatic food inspection device 100 further includes a set of handles 600 installed on two sides of the automatic food inspection device 100 so that the user may conveniently move the automatic food inspection device 100 with two hands.

Accordingly, the automatic food inspection device not only has a compact size and can be conveniently moved by the user with both hands, but also uses a propulsion device to prevent the objects to be tested, e.g. coffee beans, from accumulating on the entrance of the conveying track. One side of the U-shaped track fixed to the linear vibrator may improve the arrangement and advancement of the objects to be tested, e.g. coffee beans. The transparent tempered glass may reduce the number of rotations of the objects to be tested, e.g. coffee beans, and slow down the falling speed so as to provide the image and the configuration of the light-emitting diode light source from two sides and increase the clarity of the image. The configuration of infrared detectors and nozzles may more accurately classify the objects to be tested, e.g. coffee beans, and improve the classification quality and accuracy of the objects to be tested, e.g. coffee beans.

Although the present disclosure has been disclosed above in terms of implementation, it is not intended to limit the present disclosure. Any person with ordinary knowledge in the field may make various variations and modifications without departing from the spirit and scope of the disclosure. Therefore, the spirit and scope of the appended claims should not be limited to the description of the embodiments contained herein.

What is claimed is:

1. An automatic food inspection device, comprising:
   a feeding container for accommodating objects to be tested;
   a track conveying device connected to the feeding container to deliver the objects to be tested;
   a transparent track separated with the track conveying device to further deliver the objects to be tested; and
   an image capture module located adjacent to the track conveying device and the transparent track to capture images of the objects to be tested to judge qualities of the objects to be tested, wherein the image capture module comprises:
   a plurality of image sensors arranged on both sides of the transparent track and opposite to each other; and
   a plurality of lighting devices arranged on the both sides of the transparent track to illuminate the transparent track so as to illuminate the objects to be tested passing through the transparent track, wherein the transparent track is a transparent tempered glass track at an angle between 45 degrees and 75 degrees to a horizontal plane.

2. The automatic food inspection device of claim 1, wherein the lighting devices surround the image sensors.

3. The automatic food inspection device of claim 2, wherein each of the image sensors is equipped with 4 lighting devices surrounded the each of the image sensors.

4. The automatic food inspection device of claim 3, wherein the lighting devices are located outside a detection area of the image sensors.

5. The automatic food inspection device of claim 4, wherein the image capture module further comprises:
   a plurality of light absorbing devices surrounding the image sensors to absorb a light from the lighting devices.

6. The automatic food inspection device of claim 1, further comprising:
   an analysis control module judging qualities of the objects to be tested according to the images of the objects to be tested; and
   a screening module connected to the image capture module classifying the objects to be tested according to judgment results of the analysis control module.

7. The automatic food inspection device of claim 6, wherein the screening module comprises:
   a plurality of detectors detecting the objects to be tested while passing through; and
   a plurality of air nozzles to change moving paths of the objects to be tested when the objects to be tested are detected by the detectors and the analysis control module determines the qualities of the objects to be tested are defective.

8. The automatic food inspection device of claim 7, wherein the screening module further comprises:
   a classification box having a partition, a first storage tank and a second storage tank, wherein the partition is located between the first storage tank and the second storage tank.

9. The automatic food inspection device of claim 7, wherein the detectors comprise a plurality of infrared sensors to detect the objects to be tested while passing through.

10. An automatic food inspection device, comprising:
    a feeding container for accommodating objects to be tested;
    a track conveying device connected to the feeding container to deliver the objects to be tested;
    a transparent track separated with the track conveying device to further deliver the objects to be tested; and
    an image capture module located adjacent to the track conveying device and the transparent track to capture images of the objects to be tested to judge qualities of the objects to be tested, wherein the image capture module comprises:
    a plurality of image sensors arranged on both sides of the transparent track and opposite to each other; and
    a plurality of lighting devices arranged on the both sides of the transparent track to illuminate the transparent track so as to illuminate the objects to be tested passing through the transparent track, wherein the transparent track is an inclined transparent plate, wherein the transparent track further includes a clamping device to clamp the inclined transparent plate.

11. The automatic food inspection device of claim 10, wherein the inclined transparent plate is disposed at an angle between 45 degrees and 75 degrees to a horizontal plane.

12. The automatic food inspection device of claim 11, wherein detection areas of the image sensors are arranged on both sides of the inclined transparent plate and opposite to each other.

13. The automatic food inspection device of claim 10, wherein the lighting devices surround the image sensors.

* * * * *